United States Patent
Nelms

(10) Patent No.: US 11,519,831 B2
(45) Date of Patent: Dec. 6, 2022

(54) METHODS TO ISOLATE CELLS FROM FIXED TISSUE

(71) Applicant: THE BOARD OF TRUSTEES OF THE LELAND STANFORD JUNIOR UNIVERSITY, Stanford, CA (US)

(72) Inventor: Brad Nelms, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 58 days.

(21) Appl. No.: 17/196,681

(22) Filed: Mar. 9, 2021

(65) Prior Publication Data

US 2021/0285852 A1 Sep. 16, 2021

Related U.S. Application Data

(60) Provisional application No. 62/987,792, filed on Mar. 10, 2020.

(51) Int. Cl.
| | |
|---|---|
| *C12N 9/24* | (2006.01) |
| *G01N 1/30* | (2006.01) |
| *C12N 9/42* | (2006.01) |

(52) U.S. Cl.
CPC .............. *G01N 1/30* (2013.01); *C12N 9/2405* (2013.01); *C12N 9/2437* (2013.01); *C12N 9/2442* (2013.01); *C12Y 302/01004* (2013.01); *C12Y 302/01014* (2013.01); *G01N 2001/305* (2013.01)

(58) Field of Classification Search
CPC combination set(s) only.
See application file for complete search history.

(56) References Cited

FOREIGN PATENT DOCUMENTS

CN 110699315 * 1/2020

OTHER PUBLICATIONS

Ortiz-Ramirez, et al; An Efficient Cell Sporting Protocol for Maize Protoplasts; Current Protocols in Plant Biology; 2018; e20072, vol. 3; 9 pgs.
Kanaya, et al; Purification of Ribonuclease T1 by Affinity Chromatography; J. Biochem.; 1981; 89, 591-597.

* cited by examiner

*Primary Examiner* — Maryam Monshipouri
(74) *Attorney, Agent, or Firm* — Kilpatrick Townsend & Stockton LLP

(57) ABSTRACT

Methods and compositions are provided for isolating protoplasts from plants and other multicellular, cell-wall containing organisms with high efficiency.

2 Claims, 7 Drawing Sheets

FIG. 1A
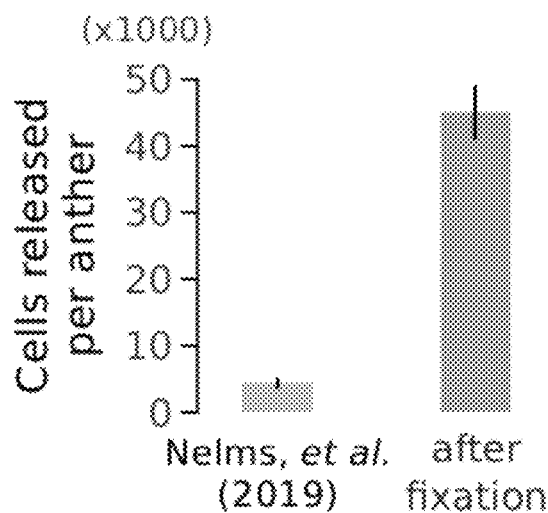
FIG. 1B
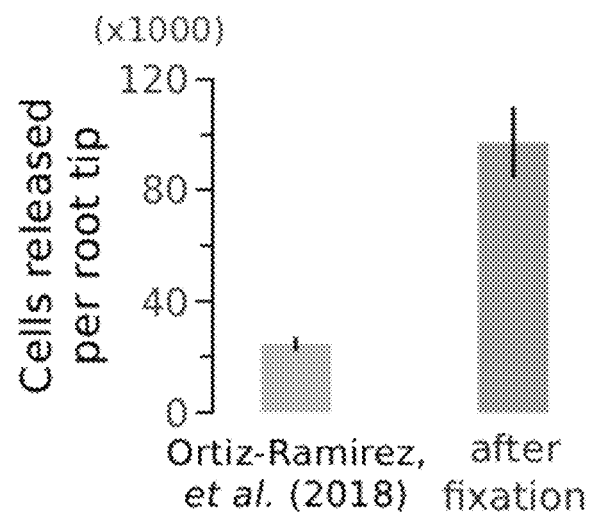
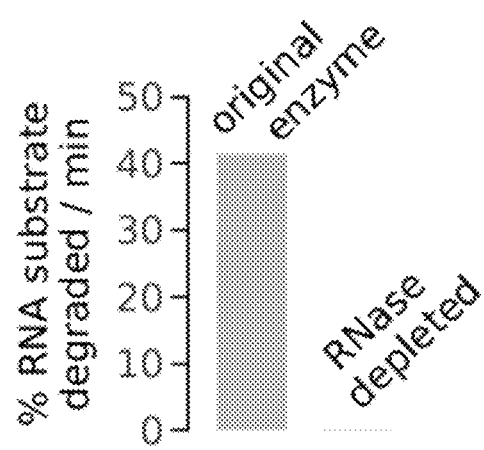
FIG. 1C

METHODS TO ISOLATE CELLS FROM FIXED TISSUE

CROSS-REFERENCE TO RELATED APPLICATION

This application claims priority to U.S. Provisional Application No. 62/987,792, filed Mar. 10, 2020, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under contract nos. 1611975 and 1754097 awarded by the National Science Foundation. The Government has certain rights in the invention.

BACKGROUND

Multi-cellular organisms contain many physiologically and morphologically distinct cell types. To understand organism function, it is often desirable to separate cells from complex tissues and perform biochemical analyses on the constituent cell types. Many approaches have been devised to purify specific cell populations for further analysis, such as fluorescence activated cell sorting (FACS); alternatively, measurements can be made on many single cells individually, and then the cell populations can be reconstructed directly from the data (e.g., single-cell RNA-sequencing). Approaches such as FACS and single-cell RNA-sequencing require tissues to first be separated into individual cells. Dissociating plant tissues is difficult or impossible for many plant organs due to the strength and resilience of the plant cell wall. In addition, single-cell RNA is often restricted by protoplast production, as cocktails of harsh enzymes are required for cell wall digestion of fresh tissue. The use of enzymes with fresh tissue results in factors that may degrade or alter the natural nucleic and proteomic state of the cells, and traditional protoplast-based methods results in cell changes during protoplasting, inconsistent cell release, and protoplast bursting in many platforms.

There is thus a need for new approaches and methods to expand the number of species and tissue types that can be isolated from plant tissues for, e.g., biochemical and genomic analysis, and that allow simpler and more efficient identification of the different cell types isolated. The present disclosure addresses these and other needs.

BRIEF SUMMARY

In one aspect, the present disclosure provides a method of isolating a protoplast from a multicellular eukaryotic organism comprising a cell wall, the method comprising: (i) fixing a tissue from the organism; (ii) incubating the tissue with an enzyme mixture with reduced RNase activity, under conditions permitting the cell wall within the tissue to be digested; and (iii) isolating the protoplast.

In one embodiment of the method, the fixing is performed by treating the tissue with paraformaldehyde, formaldehyde, glutaraldehyde, methanol, Farmer's fixative (75% ethanol, 25% acetic acid), Carnoy's fixative (60% ethanol, 30% chloroform, 10% acetic acid), or a combination thereof. In one embodiment, the mixture has been subjected to a treatment to remove at least 95% of the RNase present before the treatment. In one embodiment, the treatment comprises removing RNase from the enzyme mixture using a GMP column. In one embodiment, the mixture is substantially free of RNase or RNase activity. In one embodiment, the eukaryotic organism is a plant. In one embodiment, the plant is selected from the group consisting of maize, *Arabidopsis*, rice, soybean, wheat, barley, tomato, tree crops, other flowering plants, gymnosperms, and mosses. In one embodiment, the tissue is selected from the group consisting of tassels, anthers, roots, leaves, stems, flowers, seeds, and pollen. In one embodiment, the eukaryotic organism is a fungus.

In one embodiment, the enzyme mixture comprises an enzyme selected from the group consisting of cellulase, macerozyme, hemicellulase, pectolyase, pectinase, driselase, viscozyme, and a combination thereof. In one embodiment, the enzyme mixture comprises chitinase, glucanase, or a combination thereof. In one embodiment, the digestion step is carried out at a temperature above 30° C. In one embodiment, the temperature is about 50° C.

In another aspect, the present disclosure provides an enzyme mixture for digesting the cell wall within a eukaryotic tissue, comprising one or more enzymes selected from the group consisting of cellulase, macerozyme, hemicellulase, pectolyase, pectinase, driselase, and viscozyme, wherein the mixture has been subjected to a treatment to remove at least 95% of the RNase present before the treatment.

In one embodiment, the mixture is substantially free of RNase or RNase activity. In one embodiment, the treatment comprises removing RNase from the mixture using a GMP column.

In another aspect, the present disclosure provides an enzyme mixture for digesting the cell wall within a eukaryotic tissue, comprising one or more enzymes selected from the group consisting of chitinase and glucanase, wherein the mixture has been subjected to a treatment to remove at least 95% of the RNase present before the treatment.

In one embodiment, the mixture is substantially free of RNase or RNase activity. In one embodiment, the treatment comprises removing RNase from the mixture using a GMP column.

Other objects, features, and advantages of the present disclosure will be apparent to one of skill in the art from the following detailed description and figures.

BRIEF DESCRIPTION OF THE DRAWINGS

FIG. 1A-1C. FIGS. 1A and 1B compare the number of cells released using the method described herein vs the standard current approach (called "protoplasting"). Protoplasting (gray bars with references for specific protocols, Nelms et al. (2019) *Science*, 364(6435):52-56; Ortiz-Ramirez et al. (2018) *Current Protocols in Plant Biology*, 3, e20072) uses enzymes to digest the cell wall using fresh (unfixed) tissue. The present approach fixes the tissue first then uses the same enzymes at higher temperatures (e.g., 50° C. instead of 30° C.). FIG. 1C: The enzymes used to digest the cell wall also degrade RNA. Shown here is an assay for RNase (RNA degrading) activity before and after RNase depletion on a GMP column. During protoplasting, the cell membrane protects against RNA degradation and so there has not been the need to remove RNase activity previously. Because fixation disrupts the plasma membrane, however, the RNase activity in the enzyme blends can degrade the internal RNA. Therefore, RNase is depleted from the enzyme mixture prior to incubation. With the RNase depleted enzymes, the approach described herein greatly improves cell release, maintains cell shape, prevents changes in cell physiology during cell isolation, and reduces the need to optimize the protocol separately for every tissue.

FIG. 4A: Dissociated anther cells following fixation, incubation at 50° then mechanical disruption. FIG. 4B: Plant cells isolated from fixed tissue maintain their morphology, which can be helpful for cell identification. The insets display individual cells isolated from a fixed anther; pale blue overlays are a nuclear stain. The anther cross-section image was adapted from Chaubal et al. (2000) *American Journal of Botany,* 87(8):1193-1201 to provide a reference of normal anther cell morphology. FIG. 4C: Fixation allows for much greater cell release from maize anthers after enzymatic digestion. "Fresh, 30°" is an optimized protoplasting protocol. Dotted line, total cell number per anther as measured by confocal microscopy (Kelliher and Walbot (2011) *Developmental Biology,* 350(1), 32-49). FIG. 4D: Amplified RNA libraries after in vitro transcription from single fixed meiocytes or 'no cell' controls, measured on an Agilent Bioanalyzer. Low molecular weight density (<200 nt) is non-specific amplification that is removed by size selection during later library processing steps.

FIG. 6A shows RNase activity in 0.2% pectinase and 0.2% cellulase enzyme preparations. FIG. 6B shows that RNase activity in the protoplasting enzymes pectinase, cellulase, and driselase, and the ability of 25 mg/mL GMP to inhibit the activity. FIG. 6C shows a schematic of GMP immobilized on an agarose bead, as used in the columns used to remove RNase from the enzyme preparation as described herein. FIG. 6D shows RNase activity in protoplasting enzyme preparations at different dilutions and following passage over a GMP column.

DETAILED DESCRIPTION

1. Introduction

Figure 4A:
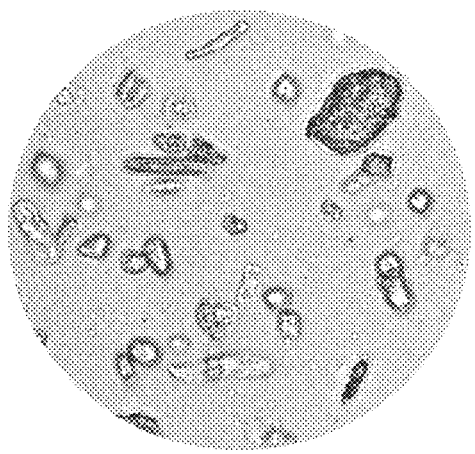
FIGS. 4A-4D. Maize anther cell release and RNA amplification.
Figure 4B:
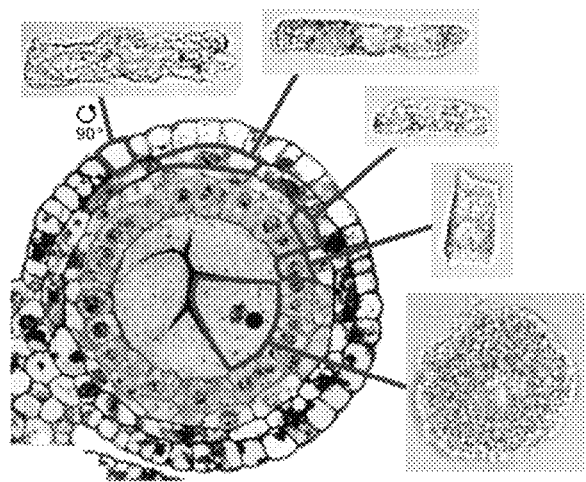
Figure 4C:
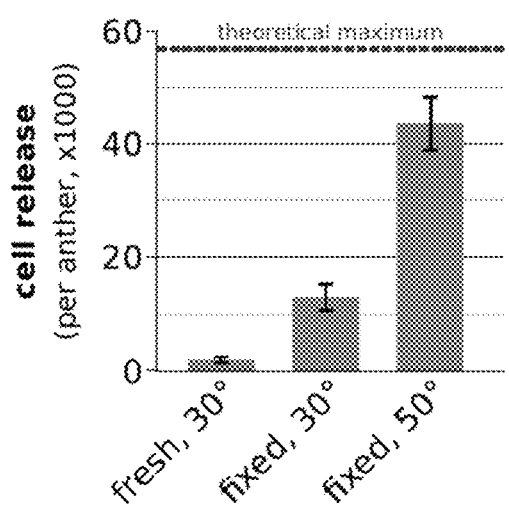
Figure 4D:
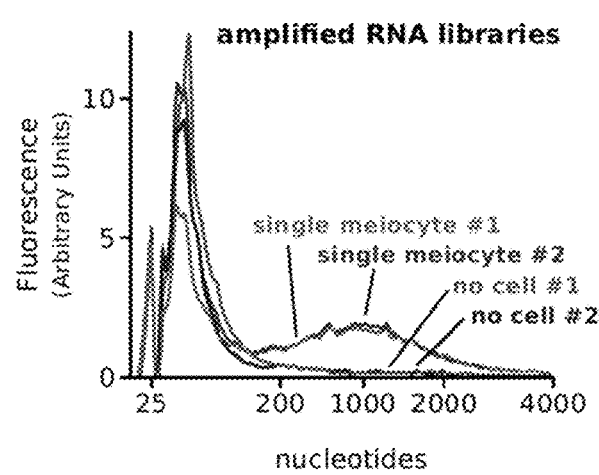
Figure 5:
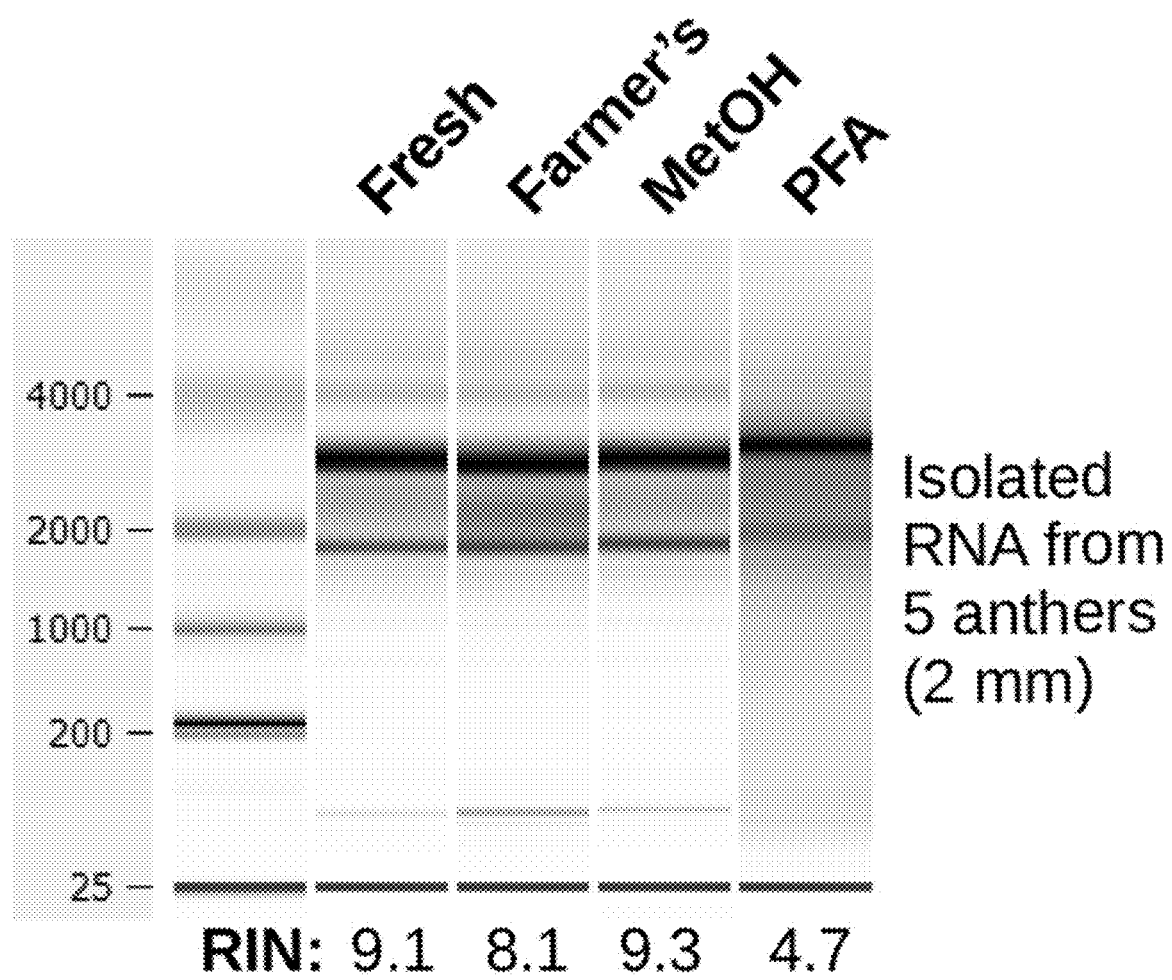
FIG. 5. Fixation preserves RNA quality. Whole anthers were either fixed in the listed fixative or flash frozen, then RNA was purified and the RNA distribution was determined on an Agilent Bioanalyzer. After fixation, the RNA quality is similar to unfixed tissue.
Figure 6A:
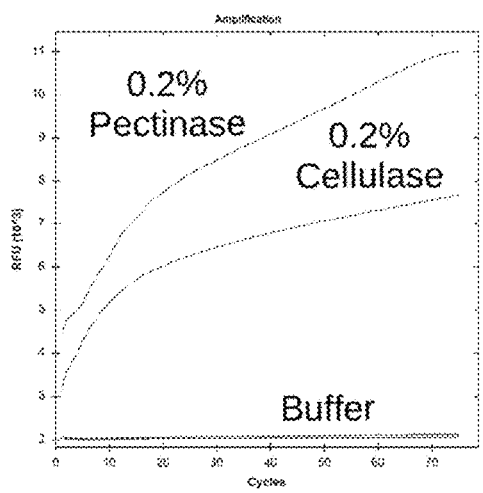
FIGS. 6A-6D.
Figure 6B:
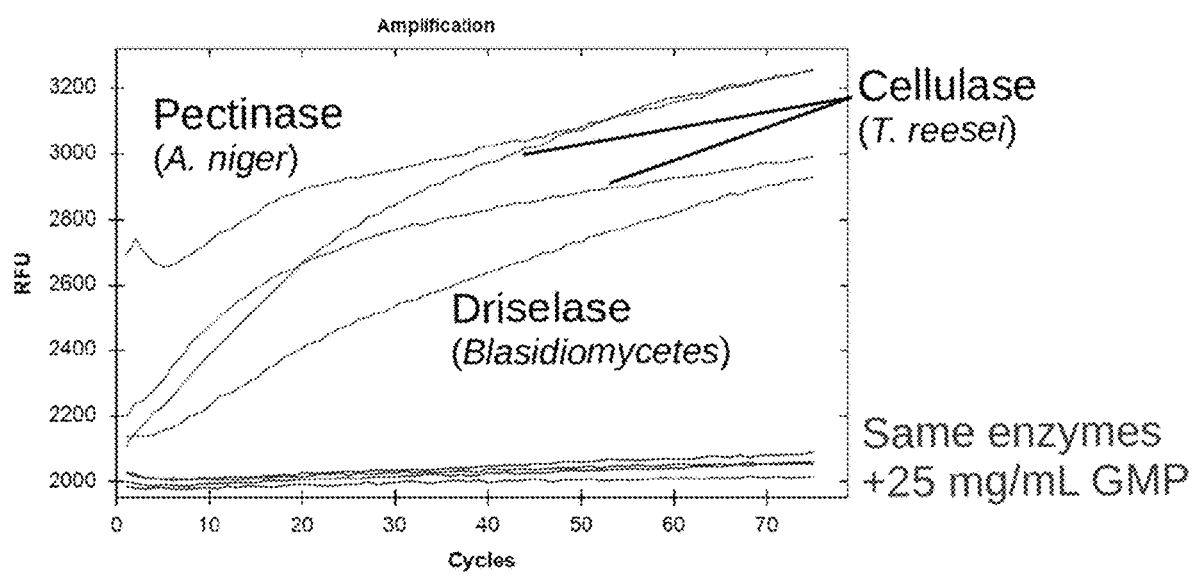
Figure 6C:
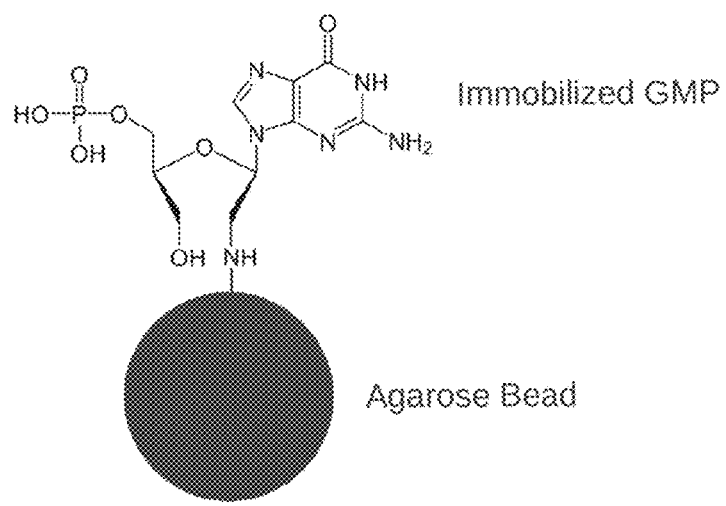
Figure 6D:
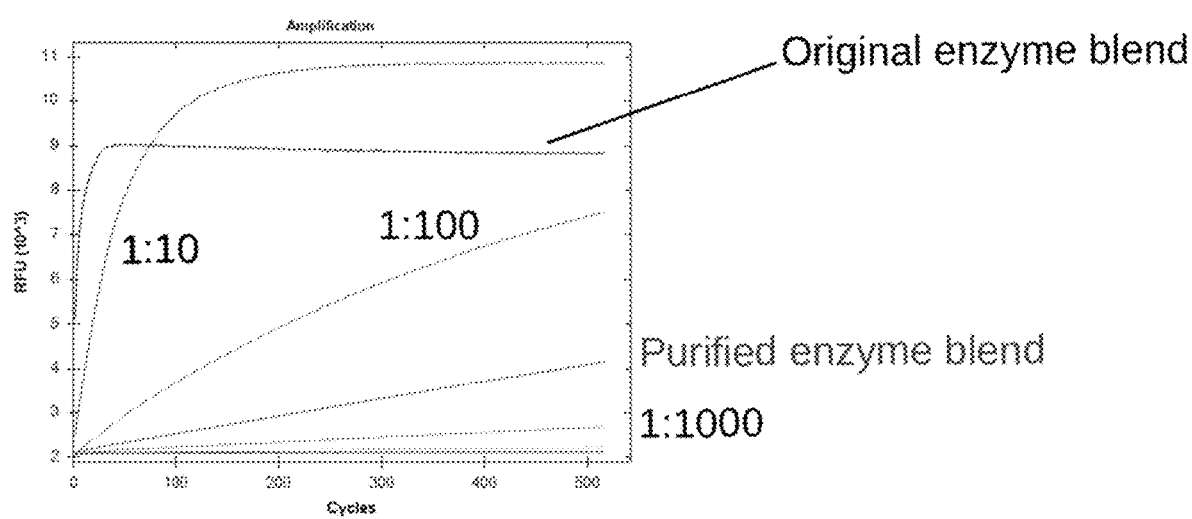

The present disclosure provides novel methods and compositions for isolating protoplasts from plants or other cell-wall-containing multicellular organisms. Traditional approaches to dissociate plant tissues use fungal enzymes to digest the cell wall and release protoplasts. The present methods represent an important improvement to this approach. In one aspect, in the present methods, instead of using fresh tissue, plant tissues are fixed prior to enzymatic digestion. Fixation mechanically stabilizes the cells and allows for much harsher digestion conditions (e.g., higher temperatures, stronger enzymatic, physical, mechanical, or chemical conditions), dramatically improving the efficiency of tissue dissociation (FIGS. 1A-1B). For instance, after fixation it is possible to reproducibly dissociate 80-100% of cells from maize anthers (a part of the flower), compared to 2%-10% using unfixed tissue (FIG. 1A). Fixation also preserves RNA quality (FIG. 5) and cell morphology to aid in identification of plant cell types; while protoplasts from fresh tissue are spherical and often hard to identify, fixed cells maintain their unique shapes after tissue dissociation and can be recognized based on morphology (FIGS. 4A-4B).

Figure 2:
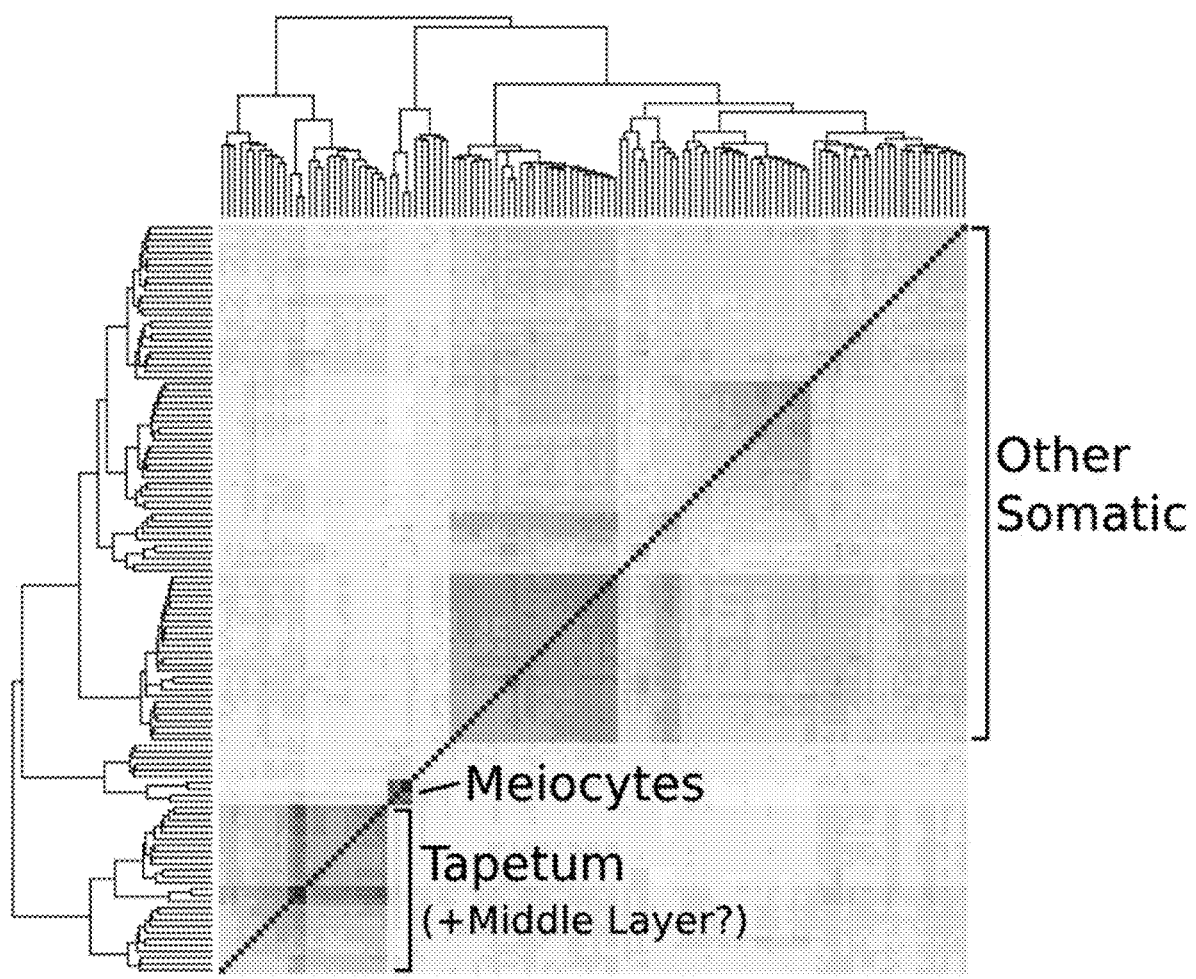
FIG. 2. A heatmap of cell-to-cell correlation for single-cell RNA-seq. Cell types can be identified and form clusters. The cells in this experiment were released using the present methods and purified by flow sorting. Alternative methods to isolate single cells, including microcapillary isolation or droplet-based sorting, would be compatible with the tissue dissociation methods described herein.

The present methods can be used for a number of applications, including for RNA-sequencing, i.e., measuring the abundance of RNAs in specific cell populations or single cells (FIG. 2). However, the RNA from fixed tissue is accessible to enzymes in solution, as fixation permeabilizes the cell membrane, and the enzymes used to digest the cell wall are complex biological mixtures that contain substantial RNase (RNA-degrading) activity. Accordingly, the present methods also comprise the use of enzyme preparations with reduced RNase activity, e.g., preparations in which RNase activity has been reduced or eliminated. In particular, RNases can be removed from diverse enzyme mixtures using, e.g., a chromatography column coupled to Guanosine Mono-Phosphate (GMP). GMP columns have been previously used to purify RNase from fungal enzyme mixtures, but have not been used to deplete RNase previously. Using the GMP column, it is possible to obtain cell wall digesting enzymes without, or with substantially reduced amounts of, RNase and therefore to dissociate fixed plant tissues without substantially harming the RNA. It will be appreciated, however, that RNase can be depleted from the present enzyme mixtures using methods other than GMP columns. In addition to RNA sequencing, the methods can be used to isolate plant or other cell types to measure other quantities of interest (e.g., proteomics, genome sequencing, DNA methylation analysis), and has potential uses whenever individual cells or cell types must be isolated from plant or other tissues. In addition to plants, the methods can also be used for other multi-cellular organisms with a cell wall, such as multi-cellular fungi.

The present methods offer several advantages over traditional methods involving the isolation of protoplasts from fresh tissue: 1) fixation allows for harsher digestion conditions, dramatically improving the efficiency of cell release and making it possible to dissociate tissues and cell types not previously accessible; 2) protoplasting often takes 1-12 hours, during which cell physiology can change. In contrast, fixation halts biological changes during tissue dissociation; 3) protoplasts are fragile and can break apart with many commonly used techniques after tissue dissociation, whereas fixed cells are more stable; and 4) fixed isolated cells maintain their morphology, which can help in identification of specific cell types. For instance, in the maize anther it is possible to identify specific somatic cell types of the anther lobe after fixation, whereas with fresh protoplasts these cell types are indistinguishable.

One other technique for isolating specific cell populations that does not require tissue dissociation is Laser-capture micro-dissection (LCM). Compared to LCM, however, fixation followed by digestion offers several advantages: 1) it does not require any specialized equipment; 2) it can provide purer cell populations in some cases: LCM has trouble separating cell types that are small or entangled with other cells, whereas cells isolated from fixed tissue are fully separated from all other cell types; and 3) LCM is difficult to use with new techniques such as single-cell RNA-sequencing.

2. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The term "protoplast" refers to a cell (e.g., a plant cell or a fungal cell), whether fresh or fixed, with the cell wall removed (e.g., digested).

3. Detailed Description of the Embodiments

Organisms and Tissues

The present methods can be used with any plant or multicellular organism comprising a cell wall. In some embodiments, the plant is a vascular plant, e.g., angiosperm, gymnosperm, fern, horsetail, or clubmoss. In some embodiments, the plant is a moss, liverwort, or hornwort. In some embodiments, the plant is selected from the group consisting of maize, rice, wheat, barley, millet, *Arabidopsis*, tomato, tobacco, citrus trees, other tree crops, soybean. In some embodiments, the multicellular organism is a fungus. Examples of fungi that can be used include, inter alia, mushrooms, toadstools, and molds.

Any tissue from the organism can be used to obtain the protoplasts. For example, from plants protoplasts can be obtained from, inter alia, leaves, stems, roots, flowers, pollen, anthers, seeds, or root nodules. The tissue can be any type of tissue, including, e.g., epidermis, vascular tissue, ground tissue, meristematic tissue, or permanent tissue, and the protoplast can be any cell type, including meiocytes, meristematic cells, parenchyma cells, collenchyma cells, epidermal cells, reproductive cells, or sclerenchyma cells.

Fixation

For fixation, the tissue is dissected from the plant or other organism and then fixed. Any fixative can be used in the methods, including cross-linking fixatives and coagulative fixatives. In some embodiments, the tissue is fixed using a cross-linking fixative such as formaldehyde, paraformaldehyde (PFA) (e.g., 4% PFA), glutaraldehyde, or neutral buffered formalin. In some embodiments, a coagulative fixative is used, such as methanol (e.g., 80% methanol), Farmer's Fixative (75% ethanol, 25% acetic acid), or Carnoy's fixative (60% ethanol, 30% chloroform, 10% acetic acid). The fixative is used in an appropriate buffer, e.g., in PBS, and for a suitable duration, e.g., 30, 60, 90, 120 minutes or longer. Following fixation, the fixed tissue is washed with buffer to remove the fixing agent, e.g., washed twice in PBS.

Tissue Dissociation

Following fixation, the tissue is incubated with enzymes to digest the cell wall and then subjected to mechanical disruption to release the protoplasts. The precise cell wall digesting enzymes will depend, e.g., on the organism and/or tissue being used. Any enzyme that digests one or more components of the cell wall of the organism can be used in the present methods. Methods of preparing tissues for dissociation and protoplast isolation are known in the art. For example, in some embodiments, the fixed tissue is cut with a razor blade or scalpel prior to incubation in order to increase access of the enzymes to cells within the tissue.

In some embodiments, e.g., for digesting the cell wall of a plant tissue, the enzyme mixture comprises one or more of the enzymes or enzyme mixtures selected from the group consisting of cellulase, macerozyme, hemicellulase, pectolyase, pectinase, driselase, and viscozyme. In some embodiments, e.g., for digesting the cell wall of a multicellular fungal organism, the enzyme mixtures comprise one or more of the enzymes or enzyme mixtures selected from the group consisting of chitinase and glucanase. The enzymes can be from any source, e.g., of fungal, animal, or bacterial origin, and can be native enzymes purified from the original source or recombinantly produced. In particular embodiments, the enzymes are of fungal or bacterial origin. The enzymes can be from, e.g., *Aspergillus niger, Aspergillus japonicas, Aspergillus aculeatus, Trichoderma reesei, Trichoderma longibrachiatum, Trichoderma viride*, Basidiomycetes, *Rhizopus, Streptomyces griseus, Trichoderma viride*, or other organisms. The enzymes can be obtained from any source, including commercial sources (e.g., Sigma Aldrich, including, but not limited to, catalog numbers C0615, P2401, H2125, and P5936). Protoplasting buffers are known in the art and can comprise, e.g., IVIES, Trehalose, $CaCl_2$), KCl and/or BSA, e.g., 10 mM MES pH 5.7, 400 mM Trehalose, 2 m mM $CaCl_2$), 10 mM KCl, 0.1% BSA.

The enzyme mixtures used for protoplast isolation according to the present methods have reduced or no RNase activity. As the enzymes used to digest the cell wall are typically complex biological mixtures of enzymes that already contain substantial RNase activity, in some embodiments the enzyme mixture has been treated to remove or reduce the amount of RNase in the mixture. For example, in some embodiments, the enzyme mixture has at least 90%, 95%, 97%, 98%, 99%, or less RNase or RNase activity than an equivalent mixture that has not been treated to reduce or eliminate RNase. In some embodiments, the enzyme mixture has less than 10%, 5%, 4%, 3%, 2%, or 1% of the original amount of RNase or RNase activity, i.e. the amount in the mixture prior to the treatment. In some embodiments, at least 90%, 95%, 96%, 97%, 98%, 99% or more of the RNase or RNase activity has been removed from the mixture. In some embodiments, the mixture has been treated to remove at least 90%, 95%, 96%, 97%, 98%, 99% or more of the RNase or RNase activity present before the treatment.

In some embodiments, the RNase is removed from the mixture using guanosine monophosphate (GMP). In particular embodiments, the RNase is removed using a chromatography column coupled to GMP, e.g., with GMP immobilized to agarose beads. Mixtures of cell wall digesting enzymes are, e.g., passed over a GMP agarose column in buffered salt solution, then the protein containing fractions that flow through the column are combined and concentrated to obtain RNase-depleted enzyme mixtures. See, e.g., Kanaya &

Uchida (1981) *J. Biochem.*, 89: 591-597, the entire disclosure of which is herein incorporated by reference. It will be appreciated, however, that any method known in the art (including, but not limited to, other column chromatography methods) can be used to remove RNase or RNase activity from the mixture.

The incubation of the fixed tissue in the RNase-depleted enzyme mixture can be carried out at any temperature, e.g., 30° C. However, due to the fixation step the tissue can resist harsher treatment than without fixation, allowing the release and isolation of a greater percentage of protoplasts from the tissue. For example, the incubation can be performed at at least about 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., or higher. In a particular embodiment, the incubation is performed at about 50° C. The incubation is performed for a suitable amount of time, e.g., about 30, 45, 60, 75, 90, 105, 120 minutes, or longer, and performed using standard methods known in the art, e.g., with gentle shaking.

Protoplast Isolation

Following incubation with the enzyme mixture, the tissue can be subjected to a mechanical force, which helps release the protoplasts. The mechanical force may be applied using any method, e.g., by pipetting the digested tissue, by applying a sheer force on the tissue such as by placing the tissue between two slides moving relative to one another, etc. It will be appreciated that, due to the increased robustness of the cells resulting from the fixation step, the mechanical force applied in this step can be stronger than that used with traditional protoplasting methods, allowing the release and recovery of greater numbers of protoplasts.

Following tissue dissociation and release of the protoplasts, the protoplasts can be washed, e.g., using protoplasting buffer without $CaCl_2$), recovered and used, e.g., for single-cell RNA-sequencing (see, e.g., Nelms & Walbot (2019) *Science*, 364(6435):52-56, the entire disclosure of which is herein incorporated by reference) or other applications. For example, the protoplasts can be manually isolated, e.g., by individually picking them up from a droplet on a slide using a syringe. In other embodiments, the protoplasts can be recovered en masse and, e.g., sorted by FACS or microfluidic technologies. In some embodiments, the identity of protoplast cells is computationally inferred after single-cell RNA sequencing.

Compositions

The present disclosure also provides compositions comprising RNase-depleted enzyme mixtures. In some embodiments, the composition comprises one or more enzymes selected from the group consisting of cellulase, macerozyme, hemicellulase, pectolyase, pectinase, driselase, and viscozyme, wherein at least 90%, 95%, 96%, 97%, 98%, 99%, or more of the RNase or RNase activity has been removed from the mixture. In some embodiments, the composition comprises one or more enzymes selected from the group consisting of cellulase, macerozyme, hemicellulase, pectolyase, pectinase, driselase, and viscozyme, wherein the mixture has been subjected to a treatment to remove at least 90%, 95%, 96%, 97%, 98%, 99%, or more of the RNase or RNase activity present before the treatment. In some embodiments, the mixture is substantially free of RNase or RNase activity. In some embodiments, the compositions comprise chitinase and/or glucanase, wherein at least 90%, 95%, 96%, 97%, 98%, 99%, or more of the RNase or RNase activity has been removed from the mixture. In some embodiments, the compositions comprise chitinase and/or glucanase, wherein the mixture has been subjected to a treatment to remove at least 90%, 95%, 96%, 97%, 98%, 99%, or more of the RNase or RNase activity present before the treatment. In some embodiments, the mixture is substantially free of RNase activity. In some embodiments, the RNase has been removed from or reduced within the mixture using a GMP column, e.g., a column comprising GMP immobilized on agarose beads. In some embodiments, the RNase or RNase activity has been removed using another method known in the art. In some embodiments, the present disclosure provides a method of preparing an enzyme mixture for digesting the cell wall of a tissue from a multicellular organism, the method comprising removing RNase from the mixture. In one embodiment, the RNase is removed using a GMP column.

Kits

In another aspect, kits are provided herein. In some embodiments, the kit comprises one or more elements for isolating protoplasts according to the present disclosure. The kit can comprise, e.g., one or more elements described herein for practicing the present methods, including an isolated protoplast, an RNase-depleted enzyme mixture, culture medium, reagents, etc.

The kits described herein can be packaged in a way that allows for safe or convenient storage or use (e.g., in a box or other container having a lid). Typically, the kits described herein include one or more containers, each container storing a particular kit component such as a reagent, an RNase-depleted enzyme mixture, a fixative, a GMP column, and so on. The choice of container will depend on the particular form of its contents, e.g., a kit component that is in liquid form, powder form, etc. Furthermore, containers can be made of materials that are designed to maximize the shelf-life of the kit components. As a non-limiting example, kit components that are light-sensitive can be stored in containers that are opaque.

In some embodiments, the kit contains one or more containers or devices, e.g., petri dish, flask, slide, syringe, for practicing the present methods. In yet other embodiments, the kit further comprises instructions for use, e.g., containing directions (i.e., protocols) for the practice of the methods described herein (e.g., instructions for using the kit for fixing and/or dissociating tissues, isolating protoplasts, depleting RNase from an enzyme mixture). While the instructional materials typically comprise written or printed materials they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD ROM), and the like. Such media may include addresses to internet sites that provide such instructional materials.

4. Examples

The following examples are offered to illustrate, but not to limit, the claimed subject matter.

Example 1. Tools for Single-Cell RNA-Seq in Maize

Figure 3:
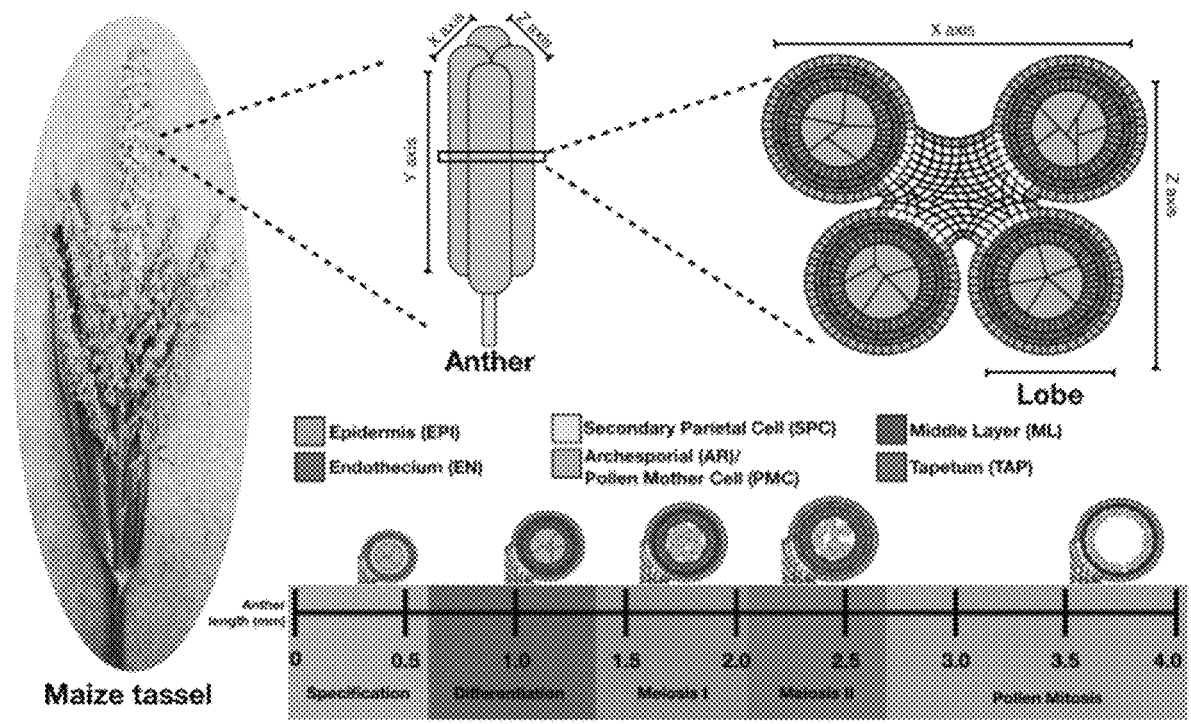
FIG. 3. Maize tassel to anther, cell layers, and cellular development. Anther length is highly correlated with development.

Fresh 2 mm maize anthers were dissected from developing tassels (FIG. 3). Anthers were either fixed in Farmer's fixative (75% ethanol, 25% acetic acid) in PBS for 2 hours then washed twice with PBS (Fixed) or put directly into cold PBS (Fresh). Fixed and fresh anthers were subjected to 2 hour incubations at 30° C. under optimized protoplasting conditions (Nelms & Walbot (2019)) and fixed anthers were also subjected to the same incubation conditions at 50° C. The anthers were mechanically disrupted via shear force between two microscope slides and the cellular release quantified with a hemocytometer. Only isolated cells were quantified. Fixed meiocytes were collected using a syringe and prepared for single-cell RNA-sequencing. Results are shown in FIGS. 4A-4D.

Example 2. Protoplasting in Maize Using RNase-Depleted Enzyme Mixtures

Fresh 2 mm maize anthers are dissected from developing tassels. Anthers are fixed in Farmer's fixative (75% ethanol, 25% acetic acid) in PBS for 2 hours then washed twice with PBS. Fixed anthers are subjected to a 2-hour incubation under optimized protoplasting conditions (Nelms & Walbot (2019)), except that the incubation is performed at 50° C. and using an enzyme mixture that has been treated to remove RNase using a GMP column (FIGS. 1C, 6A-6D). The anthers are mechanically disrupted via shear force between two microscope slides and the cellular release quantified with a hemocytometer. Fixed meiocytes are collected using a syringe and prepared for single-cell RNA-sequencing.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An enzyme mixture for digesting the cell wall within a eukaryotic tissue, comprising one or more enzymes selected from the group consisting of chitinase and glucanase, wherein the mixture has been subjected to a treatment to remove at least 95% of the RNase present before the treatment.

2. The mixture of claim 1, wherein the treatment comprises removing RNase from the mixture using a GMP column.

* * * * *